United States Patent
Taniguchi et al.

(10) Patent No.: US 7,423,019 B2
(45) Date of Patent: Sep. 9, 2008

(54) AGENT FOR INDUCING CONVERSION OF INTESTINAL CELLS INTO INSULIN-PRODUCING CELLS AND ANTIDIABETIC DRUG

(75) Inventors: Hideki Taniguchi, Ushiku (JP); Atsushi Suzuki, Kiryu (JP); Yuzuru Eto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 379 days.

(21) Appl. No.: 10/793,677

(22) Filed: Mar. 5, 2004

(65) Prior Publication Data

US 2004/0214321 A1    Oct. 28, 2004

(30) Foreign Application Priority Data

Mar. 7, 2003    (JP)    ............... 2003-061836
Oct. 17, 2003    (JP)    ............... 2003-358111

(51) Int. Cl.
*A61K 38/00* (2006.01)
*A61K 38/26* (2006.01)
*C07K 14/00* (2006.01)

(52) U.S. Cl. .................. 514/12; 530/308; 435/377

(58) Field of Classification Search .............. None
See application file for complete search history.

(56) References Cited

U.S. PATENT DOCUMENTS 6,284,727 B1    9/2001    Kim et al.
2004/0037826 A1*    2/2004    Michelsen et al. ....... 424/144.1

FOREIGN PATENT DOCUMENTS

WO    WO 98/08871    5/1998

OTHER PUBLICATIONS

Shimon, American Journal of Pharmacogenomics: genomics-related research in drug development and clinical practice, (2002) vol. 2, No. 2, pp. 129-134, Abstract PubMed ID: 12083947.*

Anonymous, Harvard health letter / from Harvard Medical School, (May 2002) vol. 27, No. 7, p. 6.*

Bataille, D. et al. "Glucagon and Related Peptides", *Annals New York Academy of Sciences*, vol. 527 pp. 168-185, 1988.

Bataille, D. et al. "Bioactive Enteroglucagon (Oxyntomodulin): Present Knowledge on Its Chemical Structure and Its Biological Activities", Peptides, vol. 2 pp. 41-44, 1981.

Mojsov, S. et al. "Insulinotropin: Glucagon-like Peptide I (7-37) Co-encoded in the Glucagon Gene Is a Potent Stimulator of Insulin Release in the Perfused Rat Pancreas", *J. Clin. Invest.*, vol. 79 pp. 616-619, 1987.

Abraham, E.J. et al. "Insulinotropic Hormone Glucagon-Like Peptide-1 Differentiation of Human Pancreatic Islet-Derived Progenitor Cells into Insulin-Producing Cells", *Endocrinology*, vol. 143(8) pp. 3152-3161, 2002.

Gutniak, M. et al. "Antidiabetogenic Effect of Glucagon-Like Peptide-1 (7-36) Amide in Normal Subjects and Patients with Diabetes Mellitus", *The New England Journal of Medicine*, vol. 326(20) pp. 1316-1322, 1992.

Ghiglione, M. et al. "How glucagon-like is glucagons-like peptide-1?", *Diabetologia*, vol. 27 pp. 599-600, 1984.

Schmidt, W.E. et al. "Glucagon-like peptide-1 but not glucagon-like peptide-2 stimulates insulin release from isolated rat pancreatic islets", *Diabetologia*, vol. 28 pp. 704-707, 1985.

Drucker, D.J. "Glucagon and the Glucagon-like Peptides", *Pancreas*, vol. 5(4) pp. 484-488, 1990.

Kojima, H., et al., "Combined Expression Of Pancreatic Duodenal Homeobox 1 And Islet Factor 1 Induces Immature Enterocytes To Produce Insulin", *Diabetes*, vol. 51, No. 5, pp. 1398-1408, (2002).

Drucker, D.J., "Glucagon-Like Peptides: Regulators Of Cell Proliferation, Differentiation, And Apoptosis", *Molecular Endocrinology*, vol. 17, No. 2, pp. 161-171, (2003).

Suzuki, A., et al., "Glucagon-Like Peptide 1 (1-37) Converts Intestinal Epithelial Cells Into Insulin-Producing Cells", *Proc. Natl. Acad. Sci. USA*, vol. 100, No. 9, pp. 5034-5039, (2003).

* cited by examiner

*Primary Examiner*—David Romeo
*Assistant Examiner*—Daniel C Gamett
(74) *Attorney, Agent, or Firm*—Nath Law Group; Susanne M. Hopkins; Ari G. Zytcer

(57) ABSTRACT

A partial peptide of a preproglucagon peptide comprising at least the amino acid sequence at positions 92-97 of a preproglucagon peptide is used as an effective ingredient of an antidiabetic drug.

1 Claim, 1 Drawing Sheet

AGENT FOR INDUCING CONVERSION OF INTESTINAL CELLS INTO INSULIN-PRODUCING CELLS AND ANTIDIABETIC DRUG

TECHNICAL FIELD

The present invention relates to an agent for inducing conversion of intestinal cells into insulin-producing cells and an antidiabetic drug that contains the inducing agent. The present invention is useful in pharmaceutical and medical fields.

BACKGROUND ART

Among lifestyle-related diseases, in particular, diabetes is considered to be one of the most serious social problems because many patients are suffering from diabetes. There are plural causes to bring this diabetes state, but the direct cause of an increase in blood sugar level greatly depends on a decrease in insulin secretion or a decrease in insulin action.

β-cells, which are distributed in the Langerhans islets of the pancreas, are responsible for insulin secretion. The β-cells secrete and release insulin into the blood when glucose stimulus is applied on the cells. Insulin acts on muscle cells, fat cells, liver cells, and so on to allow glucose in blood to be imported into these cells to keep the blood sugar level constant. When the blood sugar level is kept high owing to the diabetes state, specific complications will be developed in the retina, kidney, nerve, artery, and so on.

To date, therapeutic agents for diabetes mainly focused on two functional sites (for accelerating the insulin secretion and accelerating the insulin action) have been developed and some of them have resulted in considerable effects. However, those therapeutic methods are not more than symptomatic treatments, so that they cannot attain radical therapies even though they may improve a disease state or retard the progress of the disease state. For instance, an insulin-secretion accelerator triggers a transient increase in insulin secretion. However, it has been pointed out as a real problem that the continuous usage of the drug for a long time would exhaust β-cells to irreversibly attenuate their insulin-secreting abilities. Therefore, returning the insulin-secreting functions of β-cells (which decrease as the state of diabetes progresses) to normal is nothing but restoring the β-cells themselves to normal.

Furthermore, there are various kinds of peptide hormones in the living body, which are responsible for the glucose metabolism as in the case of insulin. Among them, glucagon-related peptides to be produced from the pancreas and digestive tract are important from the viewpoint of insulin-like blood sugar regulation. The glucagon-related peptides are synthesized at first as precursors thereof, or preproglucagon. Then, the preproglucagon is processed differently depending on the respective organs. For example, the pancreas mainly produces glucagon and the digestive tract mainly produces both glucagon-like peptide (GLP)-1 and GLP-2. Possible main physiological functions of those peptide hormones are as follows. That is, glucagon accelerates the gluconeogenesis with glycogenolysis in the liver, GLP-1 accelerates the insulin secretion (the incretin action thereof) from the pancreas, and GLP-2 regulates the functions of digestive tract (e.g., see Ann N Y Acad Sci 1988; 527: 168-85).

Among them, GLP-1 was initially identified as a 37-amino acid peptide having the amino acid sequence from position 92 to position 128 of a preproglucagon peptide (hereinafter, the peptide may be referred to as GLP-1(1-37)) (e.g., see Peptides 1981; 2 Suppl 2: 41-4). After that, it was revealed that a 31-amino acid peptide (GLP-1(7-37)) starting from histidine, the amino acid at position 7, and an amide thereof constitute the substantial material of the in vivo activation and act as incretin (e.g., see J Clin Invest 1987 February; 79 (2): 616-9 and N Engl J Med 1992 May 14; 326 (20): 1316-22). GLP-1 (7-37) or a receptor agonist thereof has been expected to be an antidiabetic drug, where the acceleration of insulin-secretion from pancreatic β-cells is provided as the functional site.

GLP-1(1-37) shows a weak activity as incretin. Thus, GLP-1(7-37) has been provided not only as an antidiabetic drug but also as a main subject in the study of incretin. In other words, under the present circumstances, GLP-1(7-37) is considered to be the original of GLP-1, while GLP-1(1-37) is simply considered to be an intermediate which is generated from the precursor peptide in the processing process (e.g., see J Clin Invest 1987 February; 79 (2): 616-9).

Recently, the action of GLP-1(7-37) has been found to act on precursor cells for β-cells to induce the differentiation therefrom so as to be differentiated as insulin-positive cells. Therefore, regenerative medical procedures, which target on the restoration of β-cells, i.e., the recovery of the pancreatic functions, have been remarked in the art (e.g., see Endocrinology 2002 August; 143 (8): 3152-61).

Mainly two approaches have been investigated. One is a method for transplanting β-cells after growing and differentiating the cells in vitro, and the other is a method of inducing the differentiation of β-cells directly from their precursor cells or inducing the differentiation of insulin-producing cells. For establishing a therapeutic method, it is indispensable to widely use the method for inducing the differentiation of β-cells.

DISCLOSURE OF THE INVENTION

An object of the present invention is to provide a novel antidiabetic drug, preferably an antidiabetic drug that effects on diabetes differently from the conventional antidiabetic drug and enables an effective remedy even in the case of a decrease in function of the pancreatic islet.

The inventors of the present invention have made an extensive study with a view to solving the problems. As a result, they have finally found out that GLP-1(1-37) induces the conversion of intestinal cells into insulin-producing cells and that the differentiated insulin-producing cells are effective to blood sugar regulation.

Specifically, the inventors have searched cells, which could be converted to insulin-positive with the action of GLP-1, from various organs on the assumption that precursor cells for β-cells are present therein as well as in the pancreas. More specifically, cells were collected from every organ in a fetal mouse and were then used in an in vitro primary culture system. Then, the cells were cultured for 8 days in the presence of GLP-1(7-37) or GLP-1(1-37), followed by staining the cells with an anti-insulin antibody to investigate the presence of positive cells.

As a result, the generation of insulin-positive cells was identified only when the cells originating from the intestine were cultured in the presence of GLP-1(1-37). This result shows the presence of precursor cells for β-cells in another organ as well as the pancreas. Furthermore, it was an unpredictable finding that GLP-1(7-37), which is the original of GLP-1, can not effect on the induction of conversion of intestinal cells into insulin-producing cells even though GLP-1(1-37) effects on the induction. This finding indicates that extrapancreatic precursor cells for β-cells, unlike pancreatic precursor cells for β-cells, are inducted by a signal molecule except GLP-1(7-37). In other words, this finding suggests the importance of a 1-6 amino acid sequence (His-Asp-Glu-Phe-Glu-Arg: SEQ ID NO: 2) at the N-terminal of GLP-1(1-37).

The present invention has been made on the basis of the above findings, and the summary of the present invention is as follows.

(1) An agent for inducing conversion of intestinal cells into insulin-producing cells, comprising a partial peptide of a preproglucagon peptide as an effective ingredient, the partial peptide comprising at least the amino acid sequence at positions 92-97 of a preproglucagon peptide.

(2) The agent for inducing conversion of intestinal cells into insulin-producing cells according to the item (1), in which the partial peptide comprises any one of following amino acid sequences (a) to (j) and has an activity to induce the conversion of the intestinal cells to the insulin-producing cells:

(a) the amino acid sequence consisting of amino acid Nos. 92-97 in SEQ ID NO: 1;

(b) the amino acid sequence consisting of amino acid Nos. 92-117 in SEQ ID NO: 1;

(c) the amino acid sequence consisting of amino acid Nos. 92-124 in SEQ ID NO: 1;

(d) the amino acid sequence consisting of amino acid Nos. 92-128 in SEQ ID NO: 1;

(e) the amino acid sequence consisting of amino acid Nos. 92-179 in SEQ ID NO: 1;

(f) the amino acid sequence consisting of amino acid Nos. 84-97 in SEQ ID NO: 1;

(g) the amino acid sequence consisting of amino acid Nos. 84-117 in SEQ ID NO: 1;

(h) the amino acid sequence consisting of amino acid Nos. 84-124 in SEQ ID NO: 1;

(i) the amino acid sequence consisting of amino acid Nos. 84-179 in SEQ ID NO: 1;

(j) the amino acid sequence which is one of the amino acid sequences (b) to (i) with substitution, deletion, insertion, or addition of one or several amino acid residues.

(3) An agent for inducing conversion of intestinal cells into insulin-producing cells, comprising a partial peptide of a preproglucagon peptide as an effective ingredient, the partial peptide comprises following amino acid sequence (k) or (l) and has an activity to induce the conversion of the intestinal cells to the insulin-producing cells:

(k) the amino acid sequence consisting of amino acid Nos. 92-128 in SEQ ID NO: 1;

(l) the amino acid sequence consisting of amino acid Nos. 92-128 in SEQ ID NO: 1 with substitution, deletion, insertion, or addition of one or several amino acid residues.

(4) An antidiabetic drug, containing the agent for inducing conversion of intestinal cells into insulin-producing cells according to any one of the items (1) to (3).

(5) An implant containing cells converted to insulin-producing cells by effecting the agent for inducing conversion of intestinal cells into insulin-producing cells according to any one of the items (1) to (3) on the intestinal cells.

(6) A method for screening an agent for inducing conversion of intestinal cells into insulin-producing cells, including the steps of:

(a) culturing the intestinal cells in the presence of a test material or the agent for inducing conversion of intestinal cells into insulin-producing cells according to any one of the items (1) to (3);

(b) determining expression of an insulin-producing cell marker for the cells after the culture; and (c) making a comparison between the expression of the marker in the presence of the test material and the expression of the marker in the presence of the agent for inducing conversion of intestinal cells into insulin-producing cells.

(7) A method for screening an inhibitor of conversion of intestinal cells into insulin-producing cells, including the steps of:

(a') culturing the intestinal cells in the presence of the agent for inducing conversion of intestinal cells into insulin-producing cells according to any one of the items (1) to (3) and a test material; and (b') determining expression of an insulin-producing cell marker for the cells after the culture.

(8) A method for searching a receptor for a partial peptide of a preproglucagon peptide having an activity to induce conversion of intestinal cells into insulin-producing cells, including the steps of:

(a") transfecting a gene originating from an animal into an animal cell; and (b") effecting the agent for inducing conversion of intestinal cells into insulin-producing cells according to any one of the items (1) to (3) on the transgenic cell obtained in the step (a") to observe binding between a peptide in the inducing agent and the transgenic cell or a change in the transgenic cell.

DETAILED DESCRIPTION OF THE INVENTION

Figure 1:
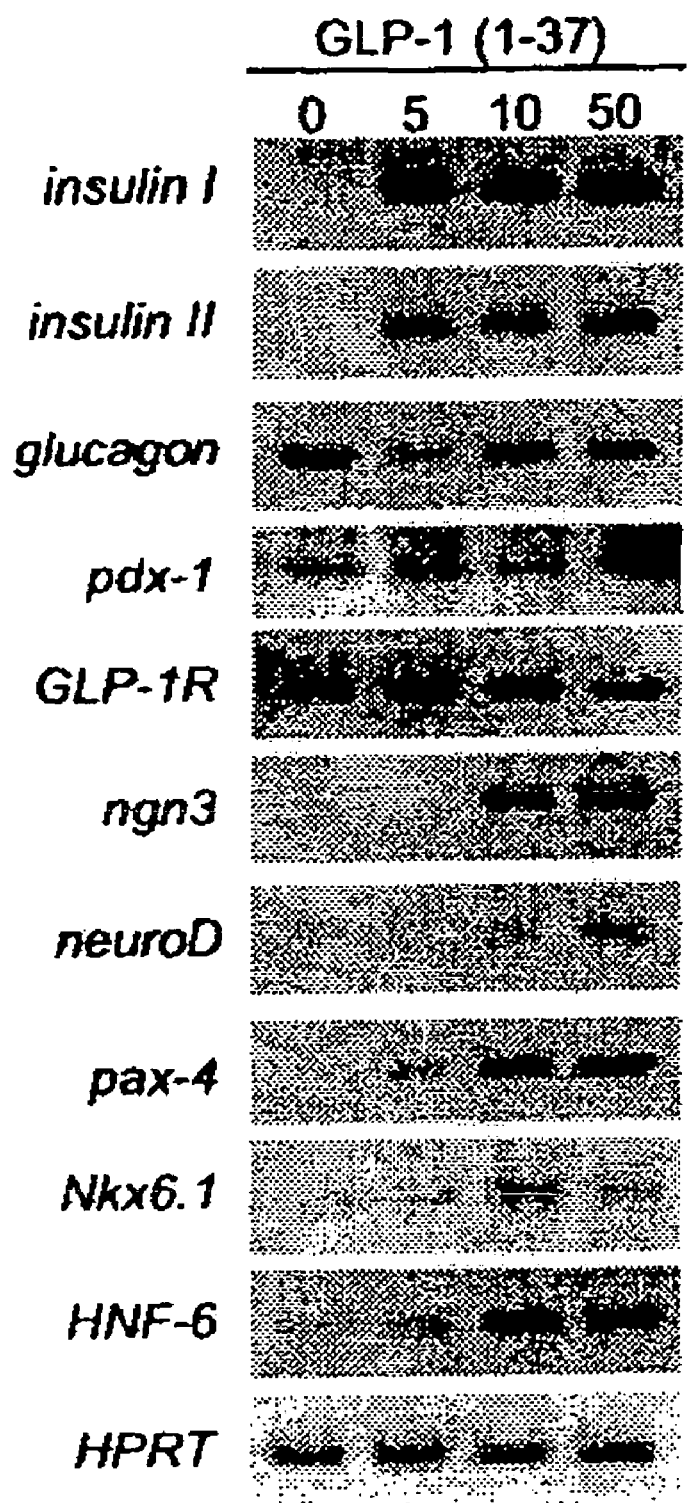
FIG. 1 is a diagram (photograph) for illustrating the results of RT-PCR, where the results show the effects of GLP-1(1-37) on cultured intestinal cells.
insulin I: preproinsulin I
insulin II: preproinsulin II
glucagon: preproglucagon
pdx-1: pancreas duodenal homeobox 1
ngn3: neurogenin 3
HPRT: hypoxanthine phosphoribosyl tranferase

Hereinafter, the present invention will be described in detail.

An agent for inducing conversion of intestinal cells into insulin-producing cells in accordance with the present invention (hereinafter, referred to as "the conversion inducer") is a partial peptide of a preproglucagon peptide, in which an active ingredient is a peptide having an inductive action for converting intestinal cells into insulin-producing cells (hereinafter, referred to as a "peptide of the present invention"). The peptide of the present invention is characterized by comprising at least the amino acid sequence (His-Asp-Glu-Phe-Glu-Arg, SEQ ID NO: 2) corresponding to positions 92 to 97 of a preproglucagon peptide. As a base of the peptide sequence of the present invention, but not particularly limited to, the sequence of the preproglucagon peptide may be of a mammal such as a human being, monkey, mouse, rat, guinea pig, rabbit, dog, cat, pig, sheep, horse, or cow, a bird such a chicken, or the like. Among them, the sequence originating from a mammal is preferable. The amino acid sequence of a human preproglucagon peptide is represented by SEQ ID NO: 1 in sequence listing (GenBank/EMBL/DDBJ accession J04040).

The peptide of the present invention is not particularly limited as far as it contains the amino acid sequence represented by SEQ ID NO: 2 described above and has an activity to induce the conversion of intestinal cells into insulin-producing cells. The peptide of the present invention may be a peptide having a partial sequence of a preproglucagon peptide or a derivative thereof with a modified part of the sequence. As described above, complicated processing has been applied on preproglucagon to generate various kinds of peptides. Among them, there are GLP-1(1-37) and MPGF (a peptide consisting of amino acids at positions 84-179 of a preproglucagon peptide), each of which is a peptide that contains the amino acid sequence represented by SEQ ID NO: 2 and is reported to have a pharmacological action (Pancreas 1990 July; 5 (4): 484-8). Furthermore, it is speculated that the rest of the various kinds of peptides includes many intermediate peptides in the processing. The present invention has found the importance of the amino acid sequence represented by SEQ ID NO: 2, so that any peptide containing the above sequence is expected to have similar effects even if it is a peptide originating from preproglucagon except GLP-1(1-37).

Specific examples of the peptide of the present invention include a peptide that has any one of following amino acid sequences (a) to (i) and has an activity to induce the conversion of intestinal cells into insulin-producing cells:

(a) the amino acid sequence consisting of amino acid Nos. 92-97 in SEQ ID NO: 1;

(b) the amino acid sequence consisting of amino acid Nos. 92-117 in SEQ ID NO: 1;

(c) the amino acid sequence consisting of amino acid Nos. 92-124 in SEQ ID NO: 1;

(d) the amino acid sequence consisting of amino acid Nos. 92-128 in SEQ ID NO: 1;

(e) the amino acid sequence consisting of amino acid Nos. 84-97 in SEQ ID NO: 1;

(f) the amino acid sequence consisting of amino acid Nos. 84-117 in SEQ ID NO: 1;

(g) the amino acid sequence consisting of amino acid Nos. 84-124 in SEQ ID NO: 1;

(h) the amino acid sequence consisting of amino acid Nos. 84-179 in SEQ ID NO: 1.

Among the peptides mentioned above, preferable is the peptide having the amino acid sequence at positions 92-128 of the preproglucagon peptide. Specifically, such a peptide may be one having the amino acid sequence of the above (d). This peptide corresponds to "GLP-1(1-37)".

In the present invention, the phrase "conversion of intestinal cells into insulin-producing cells" means that, among cells that constitute the intestinal tract, cells having a potential ability to be converted to insulin-producing cells or some of them are converted to insulin-producing cells. Thus, there is no need of converting all intestinal cells into insulin-producing cells.

The peptide of the present invention may has an amino acid sequence obtained by substitution, deletion, insertion, or addition of 1-8, preferably 1-5, more preferably 1-3 amino acid residues in one of the amino acid sequences of the above (a) to (h) as far as the peptide has the activity to induce the conversion of intestinal cells into insulin-producing cells. Furthermore, the substitution, deletion, insertion, or addition of the amino acid residues is 20% or less, preferably 15% or less, more preferably 10% or less of the total length of the peptide.

In this case, examples of an amino acid sequence which is substituted, deleted, inserted or added with one or more amino acid residue include a peptide, which is known as a GLP-1(7-37) derivative, added with the amino acid sequence of SEQ ID NO: 2. For example, there is given a GLP-1(7-37) derivative sequence, which is described in U.S. Pat. No. 6,583,111 B, added with the amino acid sequence of SEQ ID NO: 2. Examples of the GLP-1(7-37) derivative include substituted amino acids shown in the following table.

TABLE 1

| Site in GLP-1(1-37) sequence | site in SEQ ID NO: 1 | amino acid after substitution |
|---|---|---|
| 8 | 99 | Neutral amino acid |
| 9 | 100 | Neutral or acidic amino acid |
| 10 | 101 | Neutral amino acid |
| 15 | 106 | Acidic amino acid |
| 16 | 107 | Thr, Tyr |
| 18 | 109 | Lys |
| 21 | 112 | Asp |
| 22 | 113 | Ser |
| 23 | 114 | Arg |
| 24 | 115 | Arg |
| 26 | 117 | Gln, Arg, Asp, D form |
| 31 | 122 | Cys |
| 34 | 125 | D form, Arg, neutral amino acid |
| 36 | 127 | D form, Arg, neutral amino acid |

In addition, examples of the sequence in which one or more amino acid is deleted include a sequence in which 1 to 3 C-terminal amino acids are deleted.

Specific examples of the sequence include sequences of GLP-1(1-34), GLP-1(1-35), and GLP-1(1-36). Moreover, derivatives of those peptides include a peptide in which an N-terminal amino acid is acylated or alkylated, a peptide in which the N-terminal amino acid and/or the second amino acid relative to the N-terminal is substituted by a D-amino acid, and a peptide in which a histidine residue in the terminus is changed by an imidazole-based substituent. Examples of the acylated peptide include a peptide having a side chain of the Lys-34 residue added with an acyl group with linear or branched 6-10 carbon atoms. Examples of the imidazole-based substituent include the following substituents. Preferable is 4-imidazopropionyl (see U.S. Pat. No. 5,512,549 B).

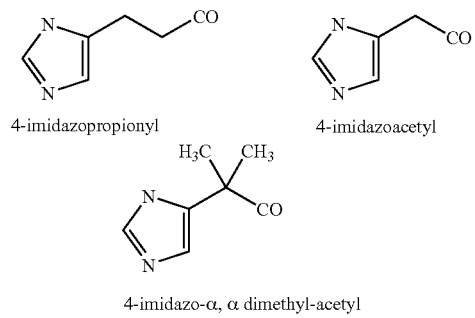

4-imidazopropionyl    4-imidazoacetyl 4-imidazo-α, α dimethyl-acetyl

In addition, derivatives of those peptides include a peptide in which a carbonyl group of the C-terminal amino acid residue is substituted by an alcohol group and a peptide in which the C-terminal amino acid residue is substituted by an amino group.

Moreover, the side chains of the terminal amino acid residue and/or other amino acid residues may have an amino group and/or carboxyl group with an appropriate protecting group. Formation and removal of the protecting group can be performed by applying a known method.

Typical examples of the amino protecting group include an acyl group, a formyl group, an acetyl group, an isopropyl group, a butoxycarbonyl group, a fluorenylmethoxycarbonyl group, and a carbobenzyloxy group. Each group suitably protects an amino group in the side chain of an N-terminal amino acid residue or a basic amino acid residue. Moreover, typical examples of the carboxyl protective group include a benzyl ester, a methyl ester, t-butyl ester, and p-nitrophenyl ester. Each group suitably protects an amino group in the side chain of a C-terminal amino acid residue or an acidic amino acid residue.

In addition, the peptide of the present invention includes salts thereof. When the peptide of the present invention can be in the form of the salt, the salt may be a pharmaceutically acceptable salt. Examples of the salt for an acidic group such as a carboxyl group in the formula can include: alkaline metal salts such as an ammonium salt, a sodium salt, and a potassium salt; salts of alkaline earth metals such as calcium and magnesium; an aluminum salt; a zinc salt; salts of organic amines such as triethylamine, ethanolamine, morpholine, pyrrolidine, piperidine, piperazine, and dicyclohexylamine; and salts of basic amino acids such as arginine and lysine. When a basic group is present in the formula, examples of the salt for the basic group can include: salts of inorganic acids such as hydrochloric acid, sulfuric acid, phosphoric acid, nitric acid, and hydrobromic acid; salts of organic carboxylic acid such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid; and salts of organic sulfonic acid such as methanesulfonic acid, benzenesulfonic acid, and p-toluenesulfonic acid.

Actions of peptides excluding those specifically represented by the sequences as described above can be identified by "a method for screening the agent for inducing conversion of intestinal cells into insulin-producing cells" of the present invention, which will be described later.

The peptide of the present invention can be produced, for example, by a method of chemically synthesizing a peptide, such as a solid phase synthesis method. In addition, the peptide of the present invention can be also produced as a recombinant peptide by making use of gene recombinant techniques using DNA that encodes the peptide to express the peptide in *E. coli*, yeast, insect cells, animal cells, or the like. The DNA can be obtained by designing the sequence thereof depending on the frequency of codon usage of the host and carrying out the conventional method of chemically synthesizing DNA.

For instance, in the case of using *E. coli*, a DNA sequence encoding the peptide of the present invention is ligated to a sequence of a promoter, such as a tryptophan synthetase operon (trp) promoter, lactose operon (lac) promoter, lambda phage promoter, tac promoter, or T7 phage promoter. Preferably, a ribosome-binding sequence such as the Shine-Dalgarno sequence (SD sequence), or a transcription termination factor is further added to the DNA sequence and then the transformation of *E. coli* is performed using an appropriate vector. The peptide of the present invention is obtained by culturing the obtained transformant under conditions that allow the promoter to serve its function. In addition, in the case of producing the peptide of the present invention as a recombinant, a methionine residue may be added to the N-terminal of the sequence selected from the above (a) to (h).

Furthermore, the peptide of the present invention may be directly expressed as a peptide itself having a target sequence or may be expressed as a fusion protein with another protein. Besides, the peptide may be accumulated as an inclusion body in the microorganism, may be accumulated as a peptide of a soluble type in the microorganism, or may be secreted to the outside of the microorganism. Examples of the fusion protein include fusion proteins with maltose binding protein, glutathione S-tranferase, and histidine tag (His-Tag).

In addition, the peptide of the present invention may be one modified to prolong the blood clearance thereof. For example, the peptide may be one in which a polyoxyalkyl polyol group is bound to a reactive group in the peptide. Preferably, the polyoxyalkyl polyol group is a polyethylene glycol group.

The peptide of the present invention can be purified from the culture by the conventional peptide purification method such as salting out, ion-exchange chromatography, or centrifugal separation. In addition, the conventional methods well known to one skilled in the art can be applied to the chemical synthesis of DNA, ligation between a DNA fragment and a vector, transformation, and so on. Those methods are described, for example, in Sambrook, J., Fritsch, E. F., and Maniatis, T., "Molecular Cloning A Laboratory Manual, Third Edition", Cold Spring Harbor Laboratory Press, (2001).

The conversion of intestinal cells into insulin-producing cells can be induced by allowing an agent for inducing conversion of intestinal cells into insulin-producing cells, the inducing agent containing the peptide of the present invention, to act on the intestinal cells. More specifically, the intestinal cells are cultured in the presence of the peptide of the present invention and if required a growth factor. The intestinal cells include cells originating from the duodenum, the small intestine (including the jejunum and ileum) and the large bowl (including the caecum, colon and rectum). Those cells are not particularly limited as far as they are collected from the intestine of a mammal. Preferably, cells are isolated from the small intestine. As a method of isolating such cells, it is not particularly limited, but for example, the method shown in the examples section can be applied. The concentration of the peptide of the present invention at the time of inducing the conversion of intestinal cells into insulin-producing cells is preferably in the range of 1 nm/l to 1,000 nm/l.

Each of the insulin-producing cells obtained as described above can be used as a therapeutic implant for a human being or animal suffering from diabetes. Therefore, the present invention provides a therapeutic method for diabetes, which includes transplanting the implant obtained in this way into the body of the human being or animal.

The conversion of intestinal cells into insulin-producing cells can be induced by administering the peptide of the present invention to a mammal such as a human being, monkey, mouse, rat, guinea pig, rabbit, dog, cat, pig, sheep, horse, or cow. The induction of the insulin-producing cells is effective for diabetes prevention and treatment. Therefore, the present invention provides a preventive or therapeutic method for diabetes using the peptide of the present invention and a preventive or antidiabetic drug containing the peptide or the conversion inducer of the present invention (hereinafter, collectively referred to as a "antidiabetic drug").

Hereinafter, the conversion inducer and the antidiabetic drug of the present invention will be described.

Dosage forms to be applied for the conversion inducer and antidiabetic drug of the present invention include an injection, sublingual agent, inhalation, transdermal poultice, tablet, capsule, fine granule, syrup, suppository, ointment, and eye drops. Among them, the injection, sublingual agent, and trandermal poulitice are preferable. In addition, depending on the dosage form, the agent may be blended with a pharmaceutically acceptable excipient such as lactose, potato starch, calcium carbonate, or sodium alginate. Furthermore, the agent may be also blended with other materials conventionally used for pharmaceuticals, for example, ingredients including proteins such as serum albumin, salts for buffer action or osmoregulation, carriers, and excipients. For the injection, a solvent to be used may be distilled water for injection, a physiological saline, Ringer's solution, or the like and a dispersant may be added to the solvent.

The peptide of the present invention to be incorporated in a conversion inducer or antidiabetic drug may be used alone or as a mixture of two or more peptides.

A dosage of the antidiabetic drug of the present invention is not particularly limited as far as the dosage serves the requirement for treating the disease. More specifically, the dosage varies depending on conditions including species, age, sexuality, body weight of the subject that requires such a treatment, an oral or parenteral (such as intravenous, subcutaneous, intramuscular, suppository, enema, ointment, poultice, sublingual, and ophthalmic) route or the like. Generally, for intravenous administration to human subjects, the dosage of the peptide of the present invention is in the range of 0.1 μg/kg to 10 mg/kg, preferably in the range of 1 μg/kg to 1 mg/kg per day per adult.

The antidiabetic drug of the present invention is effective for the treatment and prevention of diabetes and its related diseases involving a decrease in function of glucose tolerance. Those diseases include: diabetes, such as type I diabetes (insulin-dependent diabetes) and type II diabetes (non-insulin-dependent diabetes), malnutrition-related diabetes, and diabetes of another type involved in a specific disease state or symptoms; functional disorders of glucose tolerance; and gestational diabetes. However, the agent is not limited to those diseases. The agent of the present invention can be applied for a wide variety of diabetes. It is conceivable that the antidiabetic drug of the present invention will act on intestinal cells to induce the transformation thereof into insulin-producing cells to secrete insulin therefrom. Thus, the agent is expected to be effective for patients having deteriorated pancreas functions.

Moreover, the conversion inducer or antidiabetic drug of the present invention can be used in combination with a general antidiabetic drug. For example, the general antidiabetic drug includes one or a combination or mixture of two or more of the following drugs: an insulin formulation, an insulin derivative, an insulin-like agent, an insulin-secreting promoter, an insulin-resistance improving agent, a biguanide agent, a gluconeogenesis inhibitor, a sugar absorption inhibitor, a renal glucose reabsorption inhibitor, a β3-adrenaline receptor agonist, a glucagon-like peptide-1 (7-37), a glucagon-like peptide-1 (7-37) analog, a glucagon-like peptide-1 receptor agonist, a dipeptidyl peptase IV inhibitor, an aldose reductase inhibitor, an advanced glycation end-product production inhibitor, a glycogen synthetase kinase-3 inhibitor, a glycogen phosphorylase inhibitor, an anti-hyperlipemia drug, an appetite suppressant, a lipase inhibitor, an antihypertensive agent, a peripheral circulation improving drug, an antioxidant, and a therapeutic agent for diabetic neuropathy.

Examples of specific compounds of drugs to be used in combination and preferable diseases to be treated are shown below, but the present invention is not limited thereto. The specific compounds include a free form and/or other pharmaceutically acceptable salts thereof.

Examples of the insulin formulation include NPH, lente, ultralente and insulin capable of being absorbed through the lung.

The insulin derivative refers to one that has an insulin effect in a protein or peptide derived from insulin. Examples of the insulin derivative include lispro, B10Asp, and glargine.

The insulin-like agent refers to one excluding the insulin derivative, which exerts a blood sugar decrease effect by exerting an insulin physiological effect such as a sugar intake promoting effect to a cell to some extent without relying on insulin. Examples of the insulin-like agent include an insulin receptor kinase stimulator (such as L-783281, TER-17411, CLX-0901, or KRX-613) and vanadium.

The insulin-secreting promoter refers to one that exerts a blood sugar decrease effect by acting a pancreatic β cell to increase the amount of insulin secreted in blood. Examples of the insulin-secreting promoter include a sulfonylurea agent (such as tolbutamide, chlorpropamide, trazamide, acetohexamide, gliclazide, glimepiride, glipizide, or glibenclamide (glyburide)), a meglitinide (such as nateglinide, repaglinide, or mitiglinide), and an ATP-sensitive potassium channel inhibitor excluding the sulfonylurea agent and meglitinide (such as BTS-67-582).

The insulin-resistance improving agent refers to one that exerts a blood sugar decrease effect by enhancing the insulin effect in a target tissue of insulin. Examples of the insulin-resistance improving agent include a peroxisome proliferator activating receptor (PPAR) γ agonist (such as a thiazolidinedione compound including pioglitazone, rosiglitazone, troglitazone, and ciglitazone; or a non-thiazolidinedione compound including GI-262570, GW-1929, JTT-501, and YM-440), a PPAR γ antagonist (such as a bisphenol A diglycidyl ether or LG-100641), a PPAR α agonist (such as a fibrate compound including clofibrate, bezafibrate, and clinofibrate; or a non-fibrate compound), a PPAR α/γ agonist (such as KRP-297), a retinoid X receptor agonist (such as LG-100268), a retinoid X receptor antagonist (such as HX 531), and a protein tyrosine phosphatase-1B inhibitor (such as PTP-112).

The biguanide agent refers to one that exerts a blood sugar decrease effect by a gluconeogenesis inhibitory effect in the liver, an anaerobic glycolysis promoting effect in the tissue, or insulin resistance improving effect in the periphery. Examples of the biguanide agent include metformin, phenformin, and buformin.

The gluconeogenesis inhibitor refers to one that exerts a blood sugar decrease effect by inhibiting gluconeogenesis mainly. Examples of the gluconeogenesis inhibitor include a glucagon secreting inhibitor (such as M&B 39890A), a glucagon receptor antagonist (such as CP-99711, NNC-92-1687, L-168049, or BAY 27-9955), and a glucose-6-phosphatase inhibitor.

The sugar absorption inhibitor refers to one that exerts a blood sugar decrease effect by inhibiting enzymatic digestion of carbohydrates in foods in the gastrointestinal tract to inhibit or delay absorption of sugar to the body. Examples of the sugar absorption inhibitor include an α-glucosidase inhibitor (such as acarbose, voglibose, or miglitol), and an α-amylase inhibitor (such as AZM-127).

The renal glucose reabsorption inhibitor refers to one that exerts a blood sugar decrease effect by inhibiting reabsorption of sugar to the renal tubule. Examples of the renal glucose reabsorption inhibitor include a sodium-dependent glucose transporter inhibitor (such as T-1095 or phloridzin).

The β3-adrenaline receptor agonist refers to one that exerts an obesity or hyperinsulinemia improving effect by stimulating a β3-adrenaline receptor in fat to promote oxidation of a fatty acid and to consume energy. Examples of the β3-adrenaline receptor agonist include CL-316243 and TAK-677.

Examples of the glucagon-like peptide-1 (7-37) analog include exendin-4 and NN-2211. Examples of the glucagon-like peptide-1 (7-37) receptor agonist include AZM-134. Examples of the dipeptidyl peptidase IV inhibitor include NVP-DPP-728. Each of the glucagon-like peptide-1 (7-37) analog, the glucagon-like peptide-1 (7-37) receptor agonist, the dipeptidyl peptidase IV inhibitor, and the glucagon-like peptide-1 (7-37) refers to one that exerts a diabetes improving effect by imitating or enhancing a glucagon-like peptide-1 (7-37) effect in a cell.

The aldose reductase inhibitor, among those preferred to treat a diabetic complication, refers to one that decreases intracellular sorbitol, by inhibiting an aldose reductase, which is excessively accumulated by polyol metabolic pathway enhancement caused by sustaining a high blood-sugar state that is observed in a tissue in which a diabetic complication is developed. Examples of the aldose reductase inhibitor include epalrestat, tolrestat, fidarestat, and zenerestat.

The advanced glycation end-product production inhibitor, among those preferred to treat a diabetic complication, refers to one that reduces a cell disorder by inhibiting advanced glycation end product production increased by sustaining a high blood-sugar state in diabetes condition. Examples of the advanced glycation end-product production inhibitor include NNC-39-0028 and OPB-9195.

Examples of the glycogen synthetase kinase-3 inhibitor include SB-216763 and CHIR-98014. Examples of the glycogen phosphorylase inhibitor include CP-9149.

Examples of the anti-hyperlipemia drug include a hydroxymethylglutaryl coenzyme A (HMGCoA) reductase inhibitor (such as pravastatin, simvastatin, fluvastatin, or atorvastatin), a fibrate drug (such as clofibrate, bezafibrate, or simfibrate), and a bile acid excretion promoter.

Examples of the appetite suppressant include sibutramine and mazindol. Examples of the lipase inhibitor include orlistat.

Examples of the antihypertension agent include an angiotensin converting enzyme inhibitor (such as captopril or alacepril), an angiotensin II receptor antagonist (such as candesartan cilexetil or valsartan), a calcium antagonist (such as cilnidipine, amlodipine, or nicardipine), a diuretic (such as trichlormethazide or spironolactone), and a sympathetic nerve blocking agent (such as clonidine or reserpine).

Examples of the peripheral circulation improving drug include ethyl icosapentate. Examples of the antioxidant include lipoic acid and probucol.

Examples of the therapeutic agent for diabetic neuropathy include mecobalamin and mexiletine hydrochloride.

The peptide of the present invention can be used for the screening of an agent for inducing conversion of intestinal cells into insulin-producing cells. The present invention allows the intestinal cells to be converted to the insulin-producing cells, so that the screening of the conversion inducer can be performed using intestinal cells. At this time, the peptide of the present invention is used as a positive control. Specifically, the screening is performed by the following steps of:

(a) culturing the intestinal cells in the presence of a test material;

(b) determining expression of an insulin-producing cell marker for the cells after the culture; and (c) making a comparison between the expression of the marker in the presence of the test material and the expression of the marker in the presence of the conversion inducer.

The intestinal cells used in the screening process are not particularly limited as far as the cells are collected from the intestinal tract of a mammal. Preferably, however, the cells are small intestinal cells isolated by the method described in the example described later. The reaction between the cells and a test material or a conversion inducer is generally performed by culture at 35 to 40° C. for several hours to several tens of days, preferably at 36.5 to 37.5° C. for 1 to 20 days. After the reaction with the test material or the conversion inducer, the presence of conversion of the cells into insulin-producing cells and the conditions of the transformation are investigated.

The expression of an insulin-producing cell marker is measured for confirming whether the intestinal cells are converted to insulin-producing cells or not. Here, the "insulin-producing cell marker" is a protein being expressed and produced (secreted) specifically in the insulin-producing cells or a gene encoding the protein. For instance, the marker can be identified by examining the production and insulin secretion. In addition, the transcription factor group (neurogenin 3 (ngn3), neuro D/BETA 2, pax-4, Nkx 6.1, and hepatocyte nuclear factor 6 (HNF-6)) that controls the differentiation of secretory cells in the pancreas can be also used as the above marker.

The peptide of the present invention can be also used for the screening of an inhibitor of the conversion of intestinal cells into insulin-producing cells. For instance, the screening is performed by the following steps of:

(a') culturing the intestinal cells in the presence of the peptide of the present invention and a test material; and (b') determining expression of an insulin-producing cell marker for the cells after the culture.

Furthermore, the peptide of the present invention can be applied in the method of searching a receptor to the partial peptide of a preproglucagon peptide having the activity to induce the conversion of intestinal cells into insulin-producing cells. For instance, the method is performed by the following steps of:

(a'') transfecting a gene originating from an animal into an animal cell; and (b'') effecting the peptide of the present invention on the transgenic cell obtained in the step (a'') to observe binding between a peptide in the inducing agent and the transgenic cell or a change in the transgenic cell.

PREFERRED EMBODIMENTS

Hereinafter, the present invention will be described specifically with reference to the examples. However, the scope of the present invention is not limited to those examples.

EXAMPLE 1

Actions of the Peptide of the Present Invention on Cells Originating from Various Kinds of Tissues Cells originating from various kinds of tissues of a 17.5 day-old embryonal mouse were divided into a group added with GLP-1(1-37) (10 nmol/l) or GLP-1(7-37) (10 nmol/l) and a non-addition control group, and were then cultured. After the cells had been cultured for 8 days, a double stain was performed using antibodies to insulin and glucagon. Specifically, the process was performed as follows.

Specimens of pancreas, liver, stomach, duodenum, and small intestine (including the jejunum, ileum, and colon) tissues were collected from a 17.5 day-old C57BL/6 embryonal mouse under a microscope. Then, those tissues were immersed in a Hanks solution (Hanks Balanced Solution, Gibco BRL, Co., Ltd., without containing Ca) containing 5 mM of $CaCl_2$ (pH 7.4) and 0.1% of collagenase, and were then incubated at 37° C. for 10 to 20 minutes, followed by gently pipetting for digestion, respectively.

The obtained cells were washed with a culture medium and then inoculated in a 6-well plate for tissue culture at a cell density of $5 \times 10^4$ cells/$cm^2$. After 24 hours from the start of the culture, GLP-1(1-37) or GLP-1(7-37) was added to the culture. Furthermore, after the cells had been continuously cultured for 8 days, the cells were washed three times with phosphate buffer (hereinafter, referred to as "PBS") and then fixed by immersing in a 4% paraformaldehyde-phosphate buffer for 5 minutes and a 25% acetone/methanol solution for 1 minute. It should be noted that GLP-1(1-37) and GLP-1(7-37) were purchased from SIGMA.

Subsequently, each well was washed with 0.05% Tween 20/PBS, followed by immersing in 0.2% Triton X100 for 1 hour. After that, anti-insulin goat antibody (Santa Cruz) and anti-glucagon mouse antibody (Sigma) were added to each well, and the whole was incubated at 4° C. for 16 hours, followed by washing the well. Then, Alexa 488-binding anti-goat IgG donkey antibody (Molecular Probes) or Cy3-binding anti-mouse IgG donkey antibody (Jackson Immuno Research Laboratories Inc.) was added to each well, and the whole was then incubated at 4° C. for 4 hours. After the well had been washed, the cells were observed under a laser-scanning microscope (Zeiss LSM510) to investigate the production of insulin and glucagon.

Consequently, among the GLP-1(1-37) addition group, the GLP-1(7-37) addition group, and the non-addition group in the pancreas, stomach, liver, and duodenal cells, no difference could be observed with respect to the number of insulin-positive cells and glucagon-positive cells. In the intestinal cells, on the other hand, insulin-positive cells were only observed in the GLP-1(1-37) addition group. In addition, all of those insulin-positive cells were strongly glucagon-positive.

EXAMPLE 2

Influence of in vivo GLP-1(1-37) Administration on Fetal Mouse

GLP-1(1-37) (10 nmol) was intraperitoneally injected to a pregnant mouse at the same time every day over a seven-day embryonal period from day 10.5 to 17.5. After birth, tissue sections from the small and large intestine of a newborn mouse were double-stained using antibodies to insulin and glucagon. Specifically, the double stain was performed as follows.

Each tissue of the small intestine (including jejunum and ileum) and the large intestine was immersed overnight in a 4% paraformaldehyde-phosphate buffer at 4° C., followed by embedding in O.C.T. compound to prepare section samples. The section samples were dried and fixed with acetone. Subsequently, the section samples were dried overnight at −20° C. and then washed with PBS-Tween 20, followed by immersing in 0.2% Triton X100 for 1 hour. After that, using anti-insulin goat antibody (Santa Cruz) or anti-glucagon mouse antibody (Sigma), and Alexa 488-binding anti-goat IgG donkey antibody or Cy3-binding anti-mouse IgG donkey antibody, the immunostain of insulin and glucagon was carried out, respectively.

As a result, in each tissue, many insulin-positive intestinal epithelium cells were observed on the whole of the intestinal epithelium. The number of insulin positive cells in the small intestine was higher than that in the large intestine.

EXAMPLE 3

Test for Transplanting Insulin Positive Cells to Diabetes Model Mouse

The jejunum collected from a 14.5-day embryonal mouse was embedded in type I collagen gel (Nitta Gelatin Inc.) and was then grown in organ culture in the presence of 50 nM GLP-1(1-37) and 50 nM PDGF (Platelet Derived Growth Factor). The amount of insulin in the culture medium was determined using a mouse insulin-detecting kit (Shibayagi) according to the attached protocol. Consequently, the insulin secretion was observed.

The jejunum at the second day from the start of the organ culture was transplanted in the abdominal cavity of a diabetes model mouse. The mouse was changed to a type I diabetes model by the administration of 200 mg/kg streptozotocin (hereinafter, referred to as "STZ") three days before the transplantation, and the blood sugar level of the mouse was 300 to 350 mg/dl. Similarly, jejunal cells cultured in the absence of GLP-1 (1-37) were transplanted into a diabetes model mouse.

Consequently, a decrease in blood sugar level was observed only in the mouse transplanted with the jejunal cells treated with GLP-1(1-37). The blood sugar level decreased to 125-225 mg/dl after four weeks and 75-100 mg/dl after eight weeks from the transplantation.

EXAMPLE 4

Detailed Analysis of Differentiated Cells

Using a quantitative PCR method, the effects of GLP-1(1-37) on the cultured intestinal cells were analyzed in detail as described below.

<1> Concentration-Dependent Effects of GLP-1(1-37)

Four concentrations of GLP-1(1-37), 0, 5, 10, and 50 nmol/l, were prepared and the organ culture of jejunum was performed by the same way as that of Example 3. After the jejunum had been cultured for 8 days, analyzed using the RT-PCR were the expression amounts of insulin genes (preproinsulin I and preproinsulin II), transcription factor group [neurogenin 3 (ngn3), neuroD/BETA 2, pax-4, Nkx 6.1, and hepatocyte nuclear factor 6 (HNF-6)] that controls the differentiation of secretory cells in the pancreas, a GLP-1 receptor (GLP-1 R), preproglucagon, pancreas duodenal homobox 1 (pdx-1), and hypoxanthine phosphoribosyl transferase (HPRT) as a positive control.

The RT-PCR was performed according to the method described in the literature (Hepatology, 32: 1230-1239) using primers. The primers used herein were as follows.

GLP-1R (SEQ ID NOS: 3 and 4), preproinsulin 1 (SEQ ID NOS: 5 and 6), preproinsulin II (SEQ ID NOS: 7 and 8), preproglucagon (SEQ ID NOS: 9 and 10), pdx-1 (SEQ ID NOS: 11 and 12), ngn3 (SEQ ID NOS: 13 and 14), neuroD (SEQ ID NOS: 15 and 16), pax-4 (SEQ ID NOS: 17 and 18), Nkx 6.1 (SEQ ID NOS: 19 and 20), HNF-6 (SEQ ID NOS: 21 and 22), and HPRT (SEQ ID NOS: 23 and 24).

Consequently, the expression of the insulin gene was observed by the addition of a small amount (5 nmol/l) of GLP-1(1-37) (FIG. 1). In addition, matching with the insulin gene expression, observed was an increase in expression of transcription factor group for controlling the differentiation of secretory cells in the pancreas.

In the GLP-1(1-37) addition group, on the other hand, there was no change in expression of the GLP-1 receptor (GLP-1R), preproglucagon, and pancreas duodenal homeobox 1 (pdx-1), compared with those in the non GLP-1(1-37) addition group.

<2> Experiment of Inhibiting GLP-1 Function

Jejunal cells were cultured by the same way as that of paragraph <1>, except that 0, 10, 100, or 1,000 nmol/l of exendin (9-39), which was a GLP-1R antagonist, was simultaneously added together with GLP-1(1-37) (10 nmol/l). Then, the expression amounts of the insulin gene and other various kinds of genes were analyzed (a culture period of 8 days).

Consequently, the expression of preproinsulin I, preproinsulin II, and ngn3 was hardly observed. The insulin gene was found to be expressed in the intestinal cells by the function of GLP-1(1-37). On the other hand, the expression of the preproglucagon and pdx-1 was not influenced by exendin (9-39).

<3> Comparison Between GLP-1 and Other Growth Factors

In the presence or absence of GLP-1(1-37) (10 nm/l), jejunal cells were cultured by the same way as that of paragraph <1>, except that activin A, beta cellulin, hepatocyte growth factor (HGF), and epidermal growth factor (EGF), which had been reported to control the growth and differentiation of secretory cells in the pancreas, were added. Then, the expression amounts of various kinds of genes were analyzed (a culture period of 8 days).

Consequently, the high expression of preproinsulin I, preproinsulin II, and ngn 3 was observed, as far as GLP-1(1-37) was added. On the other hand, no change was found in expression of preproglucagon and pdx-1.

The above analyses have suggested that GLP-1(1-37) specifically effects on intestinal cells to alter the expression of various factors for controlling the differentiation of secretory cells in the pancreas (cascade based on ngn 3 but not pdx-1) to thereby induce the insulin gene expression in intestinal cells.

EXAMPLE 5

Blood Sugar Decrease Effect on STZ Diabetes Model Rat

GLP-1 (1-37) (80 μg/head) or PBS was intraperitoneally administered to a Wistar male rat once a day over a ten-day period from day 2-12 after birth. On the 7$^{th}$ day of the administration (9-day old), 75 mg/kg of STZ was subcutaneously administered to induce diabetes. In order to prepare normal controls, some PBS-administered rats were administered citrate buffer instead of STZ. Subsequently, the rats were allowed to ingest feed and water freely. In the 42$^{nd}$ day, blood of each rat was drawn from the tail vein and the blood sugar level was measured. The measurement of the blood sugar level was performed using the whole blood sample by the glucose oxidase method in accordance with a general method.

As shown in Table 2, the blood sugar level of the diabetes control group increased about five-fold compared to that of the normal control group, while the blood sugar level of the GLP-1(1-37) administered group decreased significantly compared to that of the diabetes control group.

TABLE 2

|  | blood sugar level |
| --- | --- |
| normal control group (n = 6) | 115 ± 8 |
| diabetes control group (n = 11) | 575 ± 99 ** |
| diabetes, GLP-1(1-37) administered group (n = 6) | 430 ± 89 ** ## |

**: $p < 0.01$ vs normal control group
: $p < 0.01$ vs diabetes control group
Tukey-Kramer's test

EXAMPLE 6

Insulin Gene Expression in Intestine of GLP-1(1-37)-Administered STZ Diabetes Model Rat GLP-1(1-37) was confirmed to have the blood sugar decrease effect, so that the presence or absence of insulin production in the intestine of the GLP-1(1-37) administered group was determined by the method described below. GLP-1(1-37)(80 μg/head) or PBS was intraperitoneally administered to each of 6 Wistar male rats once a day over a ten-day embryonal period from day 2 to 12. On the 7th day of the administration (9-day old), 75 mg/kg of STZ was subcutaneously administered to induce diabetes. In order to prepare normal controls, some PBS-administered rats were administered citrate buffer instead of STZ. Subsequently, the rats were allowed to ingest feed and water freely. On the 42nd day, autopsy was performed to collect the pancreas, stomach, intestine, and lung. After RNA was prepared from each organ using ISOGEN (NIPPONGENE), mRNA of preproinsulin I and mRNA of preproinsulin II were quantified by the RT-PCR method. Oligonuculeotides shown in SEQ ID NOS: 24 and 25 were used for preproinsulin I, and oligonuculeotides shown in SEQ ID NOS: 26 and 275 were used for preproinsulin II as PCR primers.

As a result, it was confirmed that the expressions of preproinsulin I gene and preproinsulin II gene significantly increased in the intestine. On the other hand, no expression was observed in the pancreas, stomach, and lung.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety, including the priority documents, JP 2003-61836 and JP 2003-358111.

INDUSTRIAL APPLICABILITY

The present invention provides an agent for inducing conversion of intestinal cells into insulin-producing cells, a novel antidiabetic drug, and a therapeutic method for diabetes.

What is claimed is:

1. A method of treating type 1 diabetes, consisting of: administering to a subject in need thereof an antidiabetic drug consisting of amino acid Nos. 92-128 in SEQ ID NO: 1 and optionally one or more pharmaceutically acceptable excipients, wherein conversion of intestinal cells into insulin-producing cells is induced.

* * * * *

SEQUENCE LISTING

<160> NUMBER OF SEQ ID NOS: 28

<210> SEQ ID NO 1
<211> LENGTH: 180
<212> TYPE: PRT
<213> ORGANISM: Homo sapiens

<400> SEQUENCE: 1

Met Lys Ser Ile Tyr Phe Val Ala Gly Leu Phe Val Met Leu Val Gln
 1               5                  10                  15

Gly Ser Trp Gln Arg Ser Leu Gln Asp Thr Glu Glu Lys Ser Arg Ser
             20                  25                  30

Phe Ser Ala Ser Gln Ala Asp Pro Leu Ser Asp Pro Asp Gln Met Asn
         35                  40                  45

Glu Asp Lys Arg His Ser Gln Gly Thr Phe Thr Ser Asp Tyr Ser Lys
     50                  55                  60

```
Tyr Leu Asp Ser Arg Arg Ala Gln Asp Phe Val Gln Trp Leu Met Asn
 65                  70                  75                  80

Thr Lys Arg Asn Arg Asn Asn Ile Ala Lys Arg His Asp Glu Phe Glu
                 85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 2
<211> LENGTH: 6
<212> TYPE: PRT
<213> ORGANISM: Homo sapiens

<400> SEQUENCE: 2

His Asp Glu Phe Glu Arg
  1               5

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer for
      GLP-1R

<400> SEQUENCE: 3
tgaacctgtt tgcatccttc a                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer for
      GLP-1R

<400> SEQUENCE: 4
acttggcaag cctgcatttg a                                            21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: primer for
      Insulin I

<400> SEQUENCE: 5
ctgttggtgc acttctacc                                               19

<210> SEQ ID NO 6
<211> LENGTH: 20
<212> TYPE: DNA
<213> ORGANISM: Artificial Sequence
```

```
<220> FEATURE:
<223> OTHER INFORMATION: Description of Artificial Sequence: primer for
      Insulin I

<400> SEQUENCE: 6
gcagtagttc tccagctggt                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer for
      Insulin II

<400> SEQUENCE: 7
tcaagcagca cctttgtggt t                                                  21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer for
      Insulin II

<400> SEQUENCE: 8
gttgcagtag ttctccagct g                                                  21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer for
      glucagon

<400> SEQUENCE: 9
atttactttg tggctggatt g                                                  21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer for
      glucagon

<400> SEQUENCE: 10
tgtcagtgat cttggtttga a                                                  21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer for
      pdx-1

<400> SEQUENCE: 11
ttacaagctc gctgggatca c                                                  21

<210> SEQ ID NO 12
<211> LENGTH: 21
<212> TYPE: DNA
<213> ORGANISM: Artificial Sequence
```

```
<220> FEATURE:
<223> OTHER INFORMATION: Description of Artificial Sequence: primer for
      pdx-1

<400> SEQUENCE: 12
aggtcaccgc acaatcttgc t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer for
      ngn3

<400> SEQUENCE: 13
agtgctcagt tccaattcca c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: primer for
      ngn3

<400> SEQUENCE: 14
aagaagtctg agaacaccag t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer for
      neuroD

<400> SEQUENCE: 15
ggagtaggga tgcaccggga a                                              21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: primer for
      neuroD

<400> SEQUENCE: 16
cttggccaag aactacatct gg                                             22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer for
      pax-4

<400> SEQUENCE: 17
tcctgagtga aggctctgtg aa                                             22

<210> SEQ ID NO 18
<211> LENGTH: 21
<212> TYPE: DNA
<213> ORGANISM: Artificial Sequence
```

```
<220> FEATURE:
<223> OTHER INFORMATION: Description of Artificial Sequence: primer for
      pax-4

<400> SEQUENCE: 18
aaccttaagg ctccgtgaaa t                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer for
      Nkx6.1

<400> SEQUENCE: 19
tcttctggcc cggggtgatg                                                20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer for
      Nkx6.1

<400> SEQUENCE: 20
agccgcgtgc ttcttcctcc a                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer for
      HNF-6

<400> SEQUENCE: 21
atgaccatgg cctgtgaaac t                                              21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: primer for
      HNF-6

<400> SEQUENCE: 22
attcaggtgg gcatgaggat                                                20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: primer for
      HPRT

<400> SEQUENCE: 23
ctgtaatgat cagtcaacgg c                                              21

<210> SEQ ID NO 24
<211> LENGTH: 21
<212> TYPE: DNA
<213> ORGANISM: Artificial Sequence
```

```
<220> FEATURE:
<223> OTHER INFORMATION: Description of Artificial Sequence: primer for
      HPRT

<400> SEQUENCE: 24
ggcctatagg ctcatagtgc a                                          21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: primer for
      preproinsulin I

<400> SEQUENCE: 25
gggatcttca gaccttggca                                            20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer for
      preproinsulin I

<400> SEQUENCE: 26
gcagcactga tccacaatgc                                            20

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: primer for
      preproinsulin II

<400> SEQUENCE: 27
tcctctggga gccccg                                                16

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: primer for
      preproinsulin II

<400> SEQUENCE: 28
ccaccaagtg agaaccacaa ag                                         22
```